United States Patent
Laghi

(10) Patent No.: US 6,544,292 B1
(45) Date of Patent: Apr. 8, 2003

(54) PROSTHETIC LINER WITH INTEGRAL AIR EXPULSION VALVE

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

(21) Appl. No.: 10/118,193

(22) Filed: Apr. 8, 2002

(51) Int. Cl.[7] .................................................. A61F 2/80
(52) U.S. Cl. ...................................................... 623/36
(58) Field of Search ............................. 623/36, 32, 33, 623/34, 35; 602/62, 63, 77

(56) References Cited

U.S. PATENT DOCUMENTS

| | | | | |
|---|---|---|---|---|
| 1,586,015 A | * | 1/1926 | Underwood | |
| 2,808,593 A | * | 10/1957 | Andersen | |
| 3,309,714 A | * | 3/1967 | Porten | |
| 4,822,371 A | * | 4/1989 | Jolly et al. ................... 623/32 |
| 5,201,774 A | * | 4/1993 | Greene ......................... 623/34 |
| 5,728,170 A | * | 3/1998 | Becker et al. ................. 623/37 |
| 5,980,577 A | * | 11/1999 | Radis et al. ................... 623/36 |
| 6,149,691 A | * | 11/2000 | Fay et al. ..................... 623/37 |
| 6,361,568 B1 | * | 3/2002 | Hoerner ....................... 623/32 |

* cited by examiner

*Primary Examiner*—Bruce Snow
(74) *Attorney, Agent, or Firm*—Ronald E. Smith; Smith & Hopen, P.A.

(57) ABSTRACT

A prosthetic liner having a soft gel interior and a fabric-covered exterior includes an air passageway formed in the gel near the distal end of the liner. A one-way valve is positioned between the gel and the fabric with its intake side being disposed in fluid communication with the air passageway. Air passing through the air passageway is expelled through the output side of the valve through the fabric exterior. Ambulation of a user wearing the liner on a residual limb causes expulsion of air entrapped within the liner through the one-way valve.

9 Claims, 4 Drawing Sheets

FIG. 1
FIG. 2
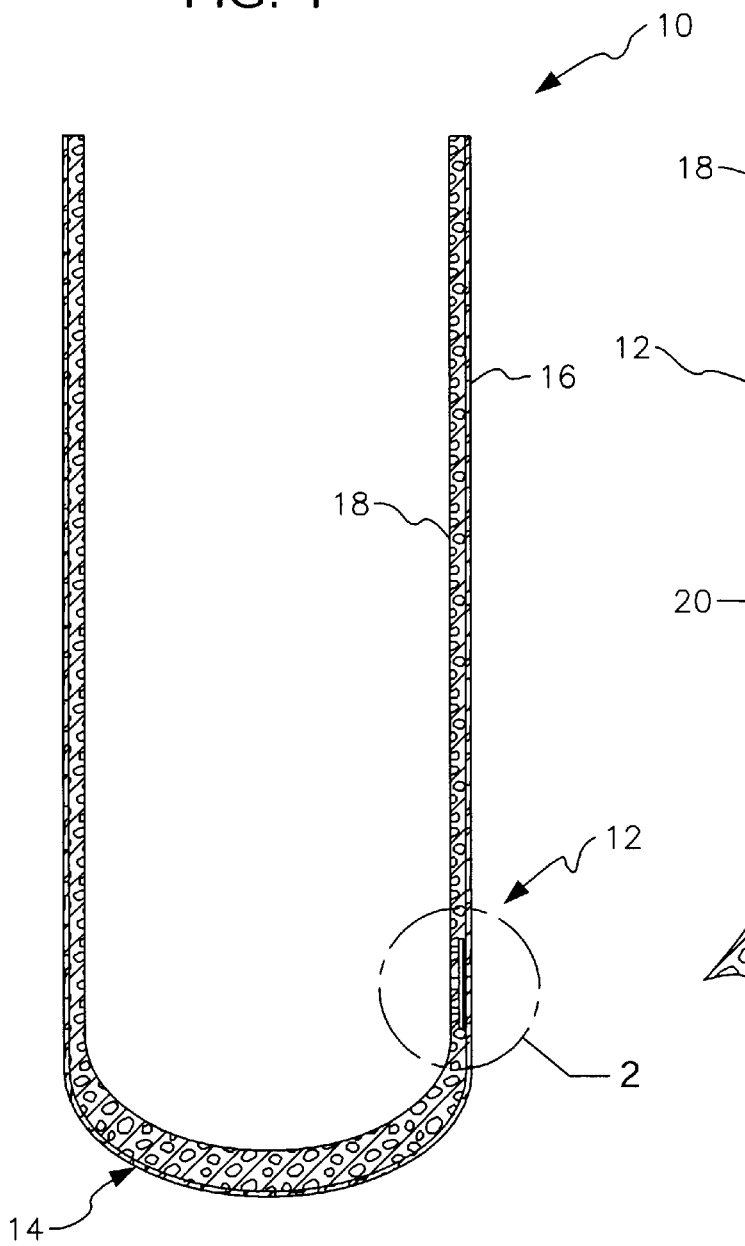
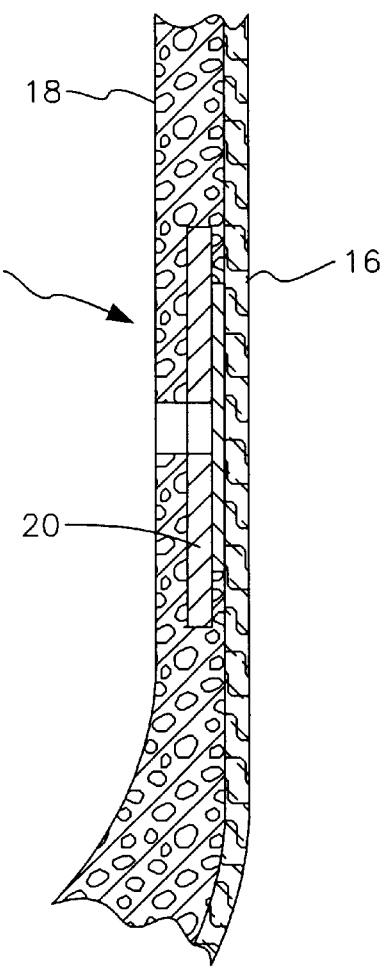

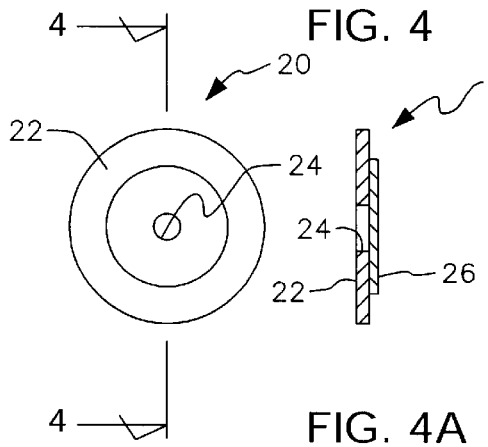
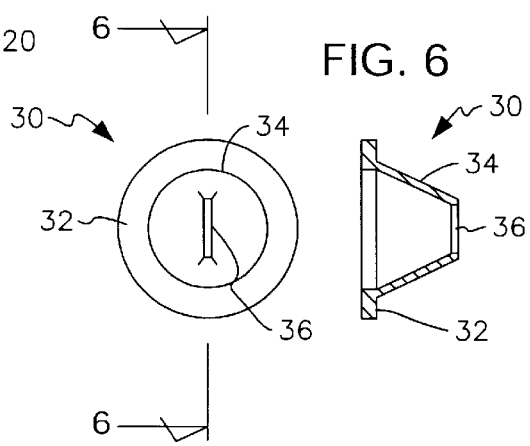
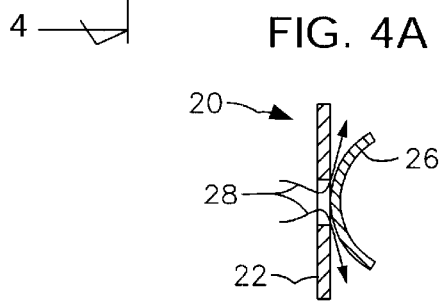
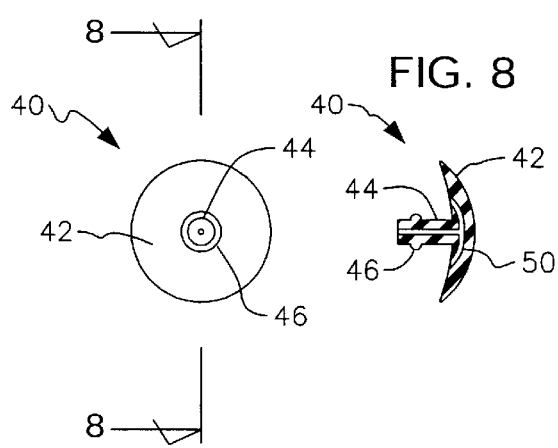
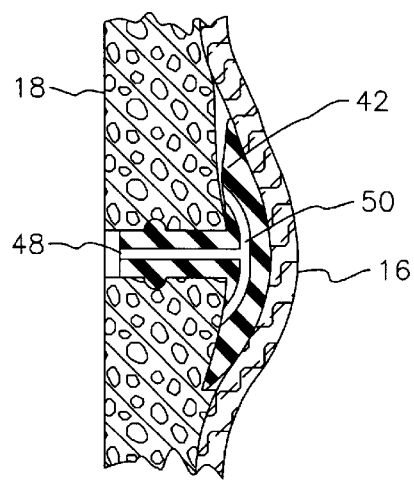

PROSTHETIC LINER WITH INTEGRAL AIR EXPULSION VALVE

BACKGROUND OF THE INVENTION

1. Field of the Invention

This invention relates, generally, to the art of prosthetics. More particularly, it relates to a cushioned liner worn on a residual limb.

2. Description of the Prior Art

A cushioned liner is worn on a residual limb, much like a sock, to provide a comfortable interface between a residual limb and a prosthetic socket. If the liner has an air-impermeable structure, it can also serve to maintain a vacuum in the space between the distal end of the liner and the distal end of the socket. Such a vacuum may be harnessed to retain the liner within the socket.

Several suppliers make cushioned liners having a gel-covered interior and a fabric exterior. The gel fits comfortably against the skin of the user and the fabric slides smoothly into the prosthetic socket.

A liner having a gel interior may be somewhat difficult to put on, especially if the user is elderly or lacks physical flexibility for some other reason. Arthritis or other similar condition can also add to the difficulty in donning a liner. To put on a gel-lined liner, it is first turned inside out so that the gel is on the outside and the fabric is on the inside. The user places the distal end of the gel against the distal end of the residual limb and progressively restores the liner to its initial, fabric-out, gel-in configuration by reversely bending the liner at the distal end thereof and rolling the bend toward the proximal end of the residual limb. The reverse bend progresses up the residual limb until the initial configuration is fully restored.

A residual limb having cicatricial tissue and scarring is more problematic because such condition tends to cause more air entrapment than normal. The liner is put on in the same way, but then the user must apply heavy finger pressure to the liner where it overlies the scarred tissue, and progressively work any air thereby liberated up to the proximal end of the liner so that it can escape. Patients who have pain or little strength and flexibility in their fingers cannot perform such procedure adequately and are therefore denied the comfort that a gel-padded liner can afford.

The purpose of the donning procedure is to eliminate air pockets between the residual limb and the liner. It is important that no air remains between the residual limb and the interior surface of the liner, particularly at the distal end of the liner. An alternating suction action, sometimes called a "milking" action, is applied to the residual limb during ambulation if air is left inside the liner. Blood may collect in the distal end of the residual limb, leading to rupturing of blood vessels or opening of sutures.

Most amputations in industrialized countries are due to vascular disease or diabetic complications. A diabetic patient may have little or no sensation in a residual limb and may be unaware that a rupturing of blood vessels or sutures has occurred. It is not unusual for such patients to be unaware for long periods of time that the distal end of their residual limb has been severely damaged. As a result, there may be a long delay in seeking help, with the result that additional surgery may then be required to remove even more of the residual limb.

What is needed, then, is a prosthetic liner that prevents the entrapment of air between a residual limb and a prosthetic liner during ambulation.

More particularly, there is a need for a liner that may be donned in the absence of a great degree of care so that a user lacking physical strength, flexibility, and manual dexterity may use such a liner without risk of causing injury to the residual limb, even if the liner entraps substantial quantities of air when the liner is put on.

However, in view of the prior art considered as a whole at the time the present invention was made, it was not obvious to those of ordinary skill in the pertinent art how such needs could be fulfilled.

SUMMARY OF THE INVENTION

The long-standing but heretofore unfulfilled need for an improved liner construction is now met by a new, useful, and nonobvious invention.

The novel liner includes an interior surface formed of a soft gel adapted to abut and overlie a user's residual limb and an exterior surface formed of a flexible fabric adapted to abut and underlie an interior surface of a prosthesis. The interior surface and exterior surface are bonded to one another substantially throughout the liner. A one-way air expulsion valve is disposed between the interior surface and the exterior surface in a preselected area of the liner. The interior surface and exterior surface are unbonded to one another in the preselected area to accommodate the one-way air expulsion valve. An air passageway is formed in the interior surface in fluid communication with an inlet of the one-way air expulsion valve and the one-way air expulsion valve is positioned such that air entrapped between a residual limb and the interior surface of the liner escapes such entrapment by flowing through the air passageway, into the inlet, and out an outlet of the one-way air expulsion valve when the user ambulates. The air from said outlet flows through the fabric into a space bordered by a distal end of the liner and a distal end of the prosthesis. Air entrapped between the residual limb and the liner is adapted to flow into said space and air in said space cannot flow in a reverse direction to re-enter the liner.

The one-way valve may take the form of a flapper valve, a duckbill valve, an umbrella valve, or any other suitable check valve means. The one-way valve is disposed at or near the distal end of the liner.

An important object of this invention is to provide a liner having a structure that allows air entrapped between a residual limb and a liner to escape before it can cause injury to the residual limb during ambulation.

A more specific object is to provide a liner where entrapped air escapes as a result of ambulation of the user.

Another more specific object is to provide a liner having a one-way air expulsion valve disposed at or near its distal end through which air flows until substantially no air remains within a space between a residual limb and the liner.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a longitudinal sectional view depicting a liner having the one-way air expulsion valve of this invention;

FIG. 2 is an enlarged view of the circled area denoted by the number 2 in FIG. 1;

FIG. 3 is a front view of a flapper valve;

FIG. 4 is a sectional view taken along line 4—4 in FIG. 3;

FIG. 4A is a sectional view like that of FIG. 4, depicting the transient displacement of a flap when air passes through said flapper valve;

FIG. 5 is a front view of a duckbill valve;

FIG. 6 is a sectional view taken along line 6—6 in FIG. 5;

FIG. 7 is a front view of an umbrella valve;

FIG. 8 is a sectional view taken along line 8—8 in FIG. 7;

FIG. 9 is a sectional view depicting the umbrella valve of FIGS. 7 and 8 when sandwiched between the gel and fabric of a liner;

DETAILED DESCRIPTION OF THE PREFERRED EMBODIMENT

Figure 10:
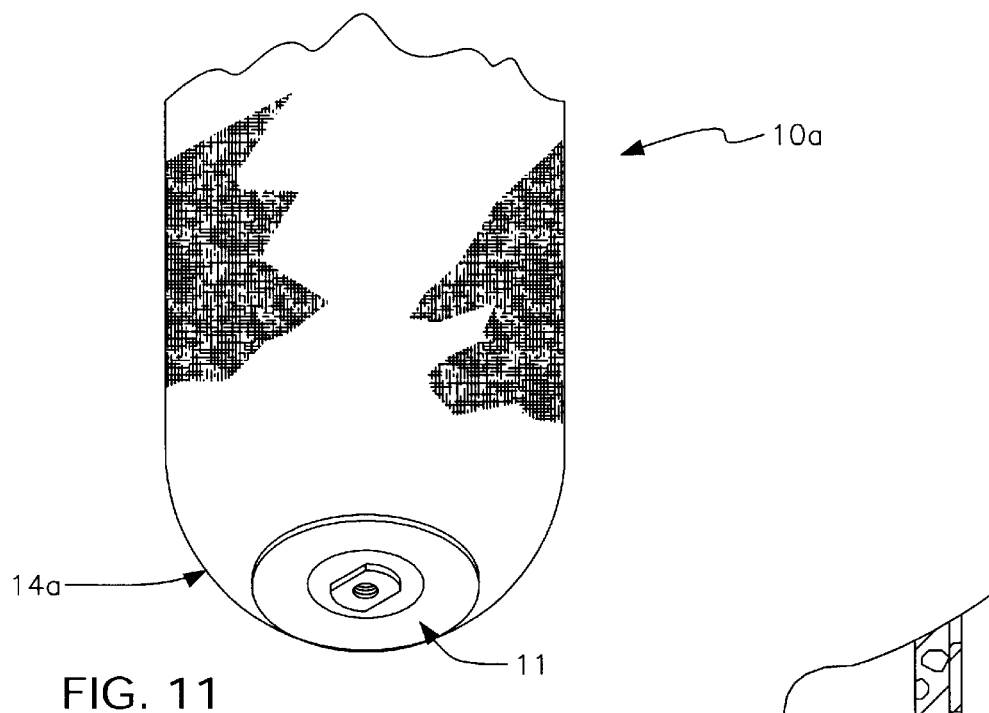
FIG. 10 is a perspective bottom view of an alternative embodiment depicting a liner having a pin-receiving attachment at its distal end adapted for coupling with a prosthetic socket.

Referring to FIG. 1, it will there be seen that the reference numeral 10 denotes an illustrative embodiment of the present invention as a whole.

Novel prosthetic liner 10 includes a one-way air expulsion valve denoted generically as 12 at or near the distal end 14 of liner 10. Liner 10 is depicted in tubular form just for ease of illustration purposes. The invention has equal applicability to all liners including generally tubular, frusto-conical, form-fitting, or custom made liners.

Liner 10 is of the type having a fabric 16 outer surface and an inner liner 18 formed of a soft gel or other suitable elastomer that does not irritate a user's skin. It may be used by above knee or below knee amputees. Fabric 16 is preferably stretchable.

Generic one-way check valve 12 may take the form of any suitable check valve means such as a flapper valve 20, depicted in FIGS. 1–4 and 4A, duckbill valve 30 as depicted in FIGS. 5 and 6, and umbrella valve 40 as depicted in FIGS. 7–9, or the like.

As indicated in connection with the embodiment of FIGS. 1 and 2, generic one-way air expulsion valve 12 is, in this first embodiment, provided in the form of flapper valve 20 that is positioned between fabric 16 and gel 18. Fabric 16 and gel 18 are bonded to one another throughout the liner except for a preselected area sufficient to accommodate the one-way valve.

The physical structure of flapper valve 20 and how it operates is perhaps better understood in connection with FIGS. 3, 4, and 4A. Valve 20 includes base 22 having a central aperture 24 formed therein. Flexible flap 26 overlies base 22 and closes central aperture 24 when said flap 26 is in repose as depicted in FIGS. 3 and 4. When the user ambulates, air remaining inside liner 10, due to a less-than-perfect donning thereof or for any other reason, is forced through central opening 24 and said flowing air lifts the peripheral edges of flexible flap 26 away from base 22 so that said air escapes through fabric 16 as indicated by directional arrows denoted 28 in FIG. 4A. Flexible flap 26 is resilient so that it resumes its FIG. 4 position of repose when air is no longer flowing therethrough. When in said position of repose, no air can re-enter the liner through said valve.

Duckbill valve 30, depicted in FIGS. 5 and 6, may be used in lieu of flapper valve 20. Duckbill valve 30 includes a base 32, frusto-conical sidewalls 34 that extend from said base, and a slit-like opening 36 through which air escapes during ambulation of the user. Opening 36 is normally closed, opening transiently only when air is forced therethrough by ambulation of a user, and returning to its closed position of repose when said air stops flowing. No air can re-enter the liner when opening 36 is in its closed configuration.

Umbrella valve 40, depicted in FIGS. 7–9, may also be used in lieu of flapper valve 20. It includes umbrella-shaped flap 42 and stem 44. Annular protrusion 46 formed in stem 44 serves to hold valve 40 in position. Passageway 48 is formed in stem 44 and provides a passageway for air trapped within the liner to escape therefrom. Said passageway 48 is in fluid communication with passageway 50 formed in flap 42 as depicted in FIGS. 8 and 9. The resiliency of umbrella part 42 allows it to be lifted when air flows outwardly from within liner 10 so that air within said liner may escape through passageways 48 and 50, and said resiliency returns said flap 42 to its position of repose when said air stops flowing. No air can re-enter liner 10 when flap 42 is in its closed configuration.

Figure 11:
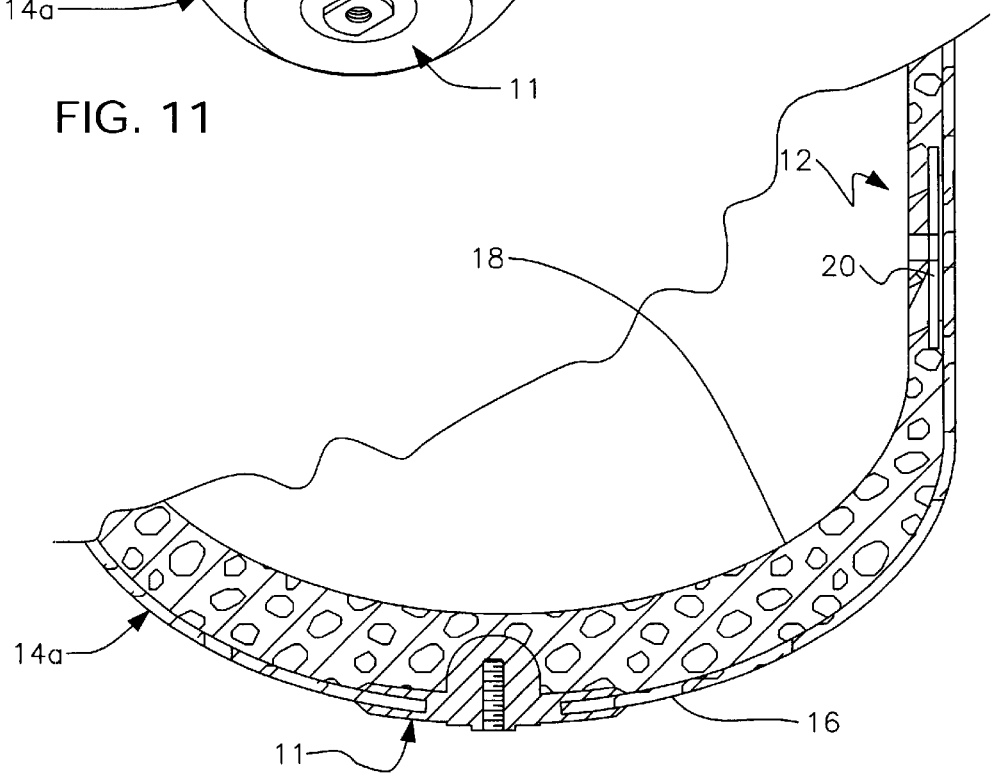
FIG. 11 is a cross-sectional view of the pin-receiving attachment of the liner of FIG. 11.

FIGS. 10 and 11 depict a liner 10a that is like liner 10 in all respects except that a distal attachment pin assembly 11 is added thereto at distal end 14a thereof. This enables engagement of distal end 14a to the distal end of a socket, not shown. When such a mechanical connection is made between a liner and a socket, no suction socket or suspension sleeve is required to interconnect the liner and socket.

Figure 12:
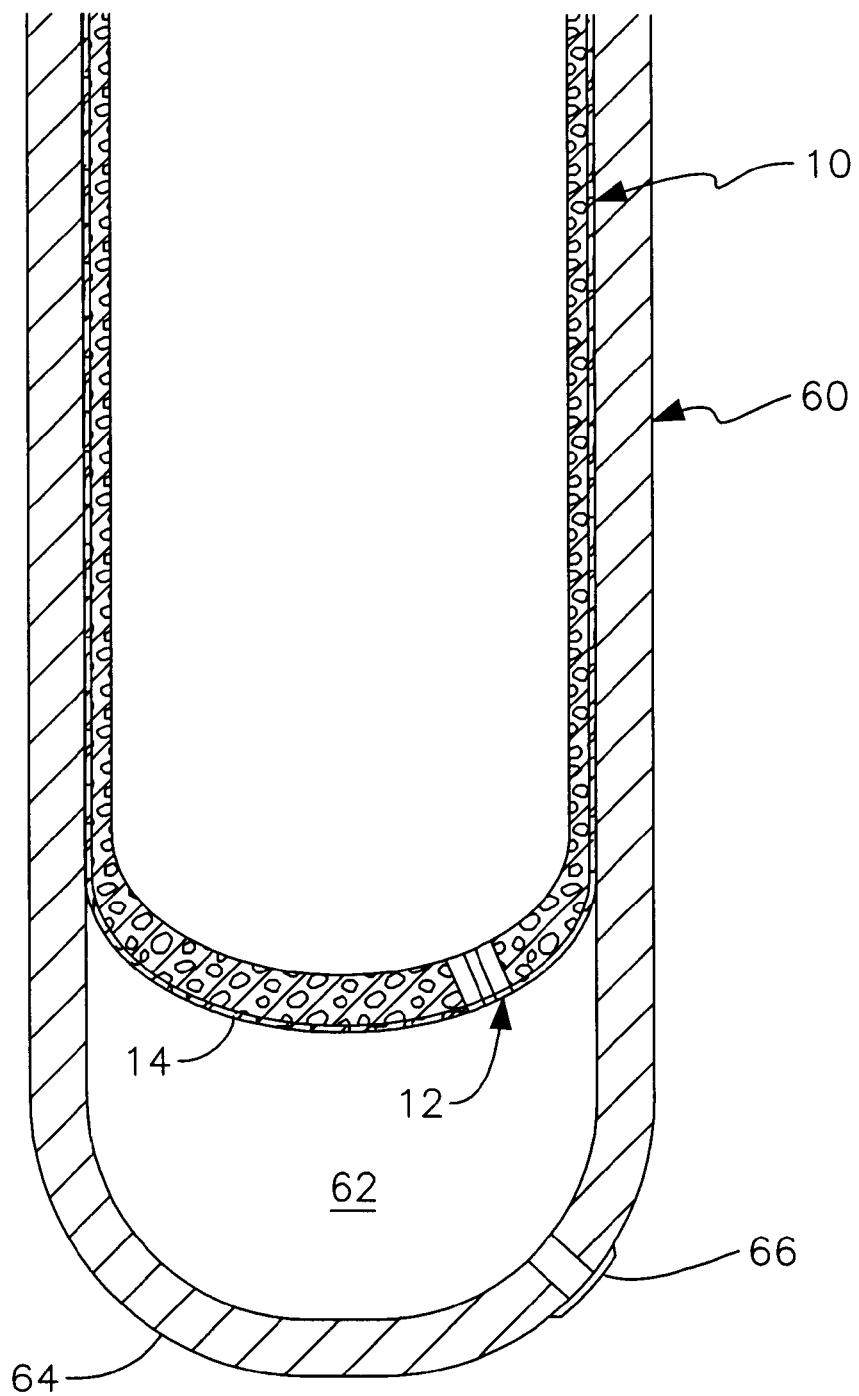
FIG. 12 is a cross-sectional view of a liner having an integral air expulsion valve when fitted into a socket having an integral air expulsion valve.

FIG. 12 depicts liner 10 when disposed in a suction socket 60. A vacuum in space 62 between distal end 14 of liner 10 and distal end 64 of socket 60 holds the liner within the socket. Fabric 16 is not air-tight so a distal attachment pin or a suspension sleeve, not shown, is employed. A suspension sleeve having a one-way air expulsion valve is preferred if a suspension sleeve is employed. Air introduced into space 62 through liner check valve 12 is expelled through socket check valve 66 into the ambient atmosphere.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A liner, comprising, an interior surface adapted to abut and overlie a user's residual limb;

an exterior surface adapted to abut and underlie an interior surface of a prosthesis;

said interior surface and said exterior surface being bonded to one another substantially throughout said liner;

a one-way air expulsion valve disposed between said interior surface and said exterior surface in a preselected area of the liner, said interior surface and exterior surface being unbonded to one another in said preselected area to accommodate said one-way air expusion valve;

an air passageway formed in the interior surface in fluid communication with the one-way air expulsion valve;

said one way air expulsion valve being positioned such that air entrapped between a residual limb and said interior, surface of said liner escapes such entrapment by flowing through the air passageway and into and through the one way air expulsion valve when the user ambulates;

whereby air entrapped between said residual limb and said liner is adapted to flow into a space bordered by a distal end of the liner and a distal end of the prosthesis and air in said space cannot flow in a reverse direction to re-enter said liner.

2. The liner of claim 1, wherein said interior surface of said liner is formed of a soft gel.

3. The liner of claim 1, wherein the exterior surface of said liner is formed of a stretchable fabric.

4. The liner of claim 1, wherein said one-way valve is a flapper valve.

5. The liner of claim 1, wherein said one-way valve is a duckbill valve.

6. The liner of claim 1, wherein said one-way valve is an umbrella valve.

7. The liner of claim 1, wherein said one-way valve is disposed at said distal end of said liner.

8. The liner of claim 1, wherein said air expulsion valve is disposed near said distal end of said liner.

9. A liner, comprising, an interior surface formed of a soft gel adapted to abut and overlie a user's residual limb;

an exterior surface formed of a flexible fabric adapted to abut and underlie an interior surface of a prosthesis;

said interior surface and said exterior surface being bonded to one another substantially throughout said liner;

a one-way air expulsion valve disposed between said interior surface and said exterior surface in a preselected area of the liner, said interior surface and said exterior surface being unbonded to one another in said preselected area to accommodate said one-way air expulsion valve;

an air passageway formed in said interior surface in fluid communication with an inlet of said one-way air expulsion valve;

said one-way air expulsion valve being positioned such that air entrapped between a residual limb and said interior surface of said liner escapes such entrapment by flowing through the air passageway and into said inlet, through the one-way air expulsion valve, and out of an outlet of said one-way air expulsion valve when the user ambulates;

said air flowing from said outlet flowing through said fabric into a space bordered by a distal end of the liner and a distal end of the prosthesis;

whereby air entrapped between said residual limb and said liner is adapted to flow into said space and air in said space cannot flow in a reverse direction to re-enter said liner.

* * * * *